(12) United States Patent
Mason et al.

(10) Patent No.: US 8,084,052 B1
(45) Date of Patent: Dec. 27, 2011

(54) CHEMICAL COMPOSITION FOR CONTROLLING INSECTS

(76) Inventors: James W. Mason, Texarkana, TX (US); Marianne L. Mason, Texarkana, TX (US)

(*) Notice: Subject to any disclaimer, the term of this patent is extended or adjusted under 35 U.S.C. 154(b) by 303 days.

(21) Appl. No.: 12/319,768

(22) Filed: Jan. 12, 2009

Related U.S. Application Data (60) Provisional application No. 61/067,147, filed on Feb. 26, 2008.

(51) Int. Cl.
| | |
|---|---|
| *A01N 25/00* | (2006.01) |
| *A01N 25/12* | (2006.01) |
| *A01N 57/10* | (2006.01) |
| *A01N 37/18* | (2006.01) |
| *A61K 35/14* | (2006.01) |
| *A61K 31/66* | (2006.01) |
| *A61K 31/145* | (2006.01) |

(52) U.S. Cl. ........ 424/405; 424/410; 424/418; 424/421; 424/529; 424/574; 514/75; 514/618

(58) Field of Classification Search .......... None
See application file for complete search history.

(56) References Cited

U.S. PATENT DOCUMENTS

| | | | |
|---|---|---|---|
| 3,220,921 A | 11/1965 | Greenbaum et al. | 167/30 |
| 3,962,461 A | 6/1976 | Brown, Jr. et al. | 424/352 |
| 4,320,130 A | 3/1982 | Balsley et al. | 424/251 |
| 4,460,606 A | 7/1984 | Bettarini et al. | 424/341 |
| 4,540,711 A | 9/1985 | Bettarini et al. | 514/720 |
| 4,874,611 A | 10/1989 | Wilson et al. | 424/410 |
| 4,985,413 A | 1/1991 | Kohama et al. | 514/79 |
| 5,094,853 A | 3/1992 | Hagarty | 424/405 |
| 5,104,658 A | 4/1992 | Hagarty | 424/405 |
| 5,116,618 A | 5/1992 | Hagarty | 424/405 |
| 5,480,638 A | 1/1996 | Erwin | 424/84 |
| 5,618,565 A | 4/1997 | Thomas | 424/717 |
| 5,679,365 A * | 10/1997 | Henderson et al. | 424/409 |
| 5,850,707 A * | 12/1998 | Fell et al. | 43/131 |
| 5,939,061 A | 8/1999 | Vail et al. | 424/84 |
| 6,153,181 A | 11/2000 | Nelson et al. | 424/84 |
| 6,228,806 B1 * | 5/2001 | Mehta | 504/117 |
| 6,831,104 B2 | 12/2004 | Taylor | 514/693 |
| 6,916,469 B2 | 7/2005 | Rojas et al. | 424/84 |

OTHER PUBLICATIONS

Farrar (Agricultural and Food Chemistry 1953, 1(14) 875-876).*

* cited by examiner

*Primary Examiner* — Ernst Arnold (74) *Attorney, Agent, or Firm* — Keisling & Pieper PLC; Trent C. Keisling; Stephen D. Schrantz

(57) ABSTRACT

The invention herein provides for an improved pesticide that includes at least one attractant, at least one plant growth stimulator and an insecticide. The pesticide eradicates fire ants and promotes the destruction of empty nests by subsequent plant growth.

9 Claims, 4 Drawing Sheets

CHEMICAL COMPOSITION FOR CONTROLLING INSECTS

CROSS-REFERENCE TO RELATED APPLICATIONS

This application claims priority to and is a continuation-in-part of U.S. provisional application Ser. No. 61/067,147, filed Feb. 26, 2008.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document may contain materials that are subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

FIELD OF THE INVENTION

The invention relates in general to a composition and method for forming an insecticide, and more particularly to a composition and method for forming a fire ant (i.e. Solenopsis saevissima v. richterii) bait insecticide. Known art may be found in U.S. Class 424, subclasses 514 and 84 as well as others.

BACKGROUND OF THE INVENTION

As will be recognized by those skilled in the art, fire ants have become an increasingly irritable pest, especially in all global temperate zones including the southern United States. These insects are quite aggressive and deliver an especially bothersome bite. These ants, scientifically named Solenopsis saevissima v. richterii, but more commonly simply called fire ants, migrated into the United States from South America during the early 1900's. The rate at which the fire ants have been spreading has increased exponentially and it has been calculated that in the U.S., fire ants will infest significant geographic regions all across the southern U.S. by 2010. The phenomenon of global warming will only tend to increase that rate of expansion and geographical impact. The infestation into populated regions has caused incalculable problems which have, in the extreme, been fatal. Moreover, the damage fire ants cause to agricultural crops, golf courses and individual lawns has grown significantly as their habitable range has increased during recent years. Thus, this pest has become a large problem for everyone across its range. Many proposals have been put forth to deal with the problem.

Many attack the fire ant problem by using high concentrations of toxic chemicals, which kill a wide variety of ants, insects, rodents and other species that may be beneficial or otherwise desirable. The amount of money spent on this problem is significant, and there is an ongoing quest for better, more effective pesticides. In fact, there is a wide variety of commercially available pesticides that have been unsuccessful in eliminating the problem.

A problem that can be vexing with eliminating fire ant infestations is the reclamation of extinct fire ant mounds by new fire ant infestations. It can take months or even years before native plants or weathering breaks down extinct mounds. Thus, a fire ant pesticide that efficiently eradicated entire colonies while also simultaneously promoting plant growth into the relinquished mounds to help break them down would be desirable. Another consideration for an improved fire ant pesticide is that it be relatively safe from unintended consequences while being highly effective at eliminating fire ant infestations. Another important consideration is that the composition be quickly rainproof so that subsequent wettings do not adversely affect the efficacy of the composition. Yet another important consideration is that the composition resists clumping when exposed to high humidity conditions, as are commonly present in most of the world's temperate regions during the summer months. An important consideration is that the composition may be economically spread by broadcasting it around and about the fire ant mound to be eradicated. Another important consideration is that the pesticide promotes replacement plant growth to help break up the fire ant mound to thereby prevent reinfestations.

Internal testing of this invention proved that fire ants could be eradicated with use of a highly organic mixture. Our success was proven by an industry respected third-party testing process, Texas A&M University AgriLIFE Extension office. Dr. Bastiaan 'Bart' M. Drees, Professor, Extension Entomologist and Regents Fellow, Department of Entomology, Texas A&M University was contacted in 2007 to conduct testing. Extensive research testing was conducted against one of the world's leading industry products, Ortho® Orthene® (containing 50% chemical acephate) and this testing substantiated our internal test findings. Report findings included that this invention uses less active ingredient to treat ant mounds than does Ortho® Orthene® (1 tablespoons of Ortho® Orthene® containing 50% acephate used 0.5 tablespoons of acephate per mound, whereas 4 tablespoons of "Fire Ant Hayter Bait" containing 4% acephate used 0.16 tablespoons acephate per mound). Therefore, use of this invention results in lower amounts of active chemical ingredient applied to the environment. Fire Ant Hayter Bait demonstrated greater efficacy in both percentages of mound eradications and in colony population elimination. The full test reports from Texas A&M University may be compared in subsequent text of this application.

Examples of known art that fail to adequately address the foregoing considerations include U.S. Pat. No. 4,985,413 issued to Kohama et al. on Jan. 15, 1991, which discloses a poison bait for control of noxious insects. A composition which comprises (a) at least one insecticide selected from the group consisting of organic phosphorous insecticides, carbamate insecticides and pyrethroid insecticide, (b) crystalline cellulose and (c) crop product powders evaporated with (d) an essential oil and (e) a saccharide respectively in amounts of 0.1 to 10.0% by weight and 10.0 to 40.0% by weight based on the total weight of the composition, which is useful as a bait for the control of noxious insects. This composition is not believed to be quickly rainproof nor economical to broadcast. The composition is not believed to promote replacement plant growth to help break up the fire ant mound to thereby prevent reinfestations.

U.S. Pat. No. 5,480,638 issued to Erwin on Jan. 2, 1996, discloses an insecticide bait composition. A powdered insecticide bait composition which includes powdered dry pet food, powdered pyrethrin or pyrethroid and boric acid killing ingredients and a powdered clay drying agent. A method for preparing the composition, including the steps of grinding the dry pet food into a powder, adding the powdered pyrethrin and boric acid killing ingredients to the pet food granules and thoroughly mixing the ingredients. The resulting powdered mixture can be sprinkled around the baseboards of a structure to kill roaches or other scavenging insects and on ant mounds to kill ants, including fire ants. An additional step in preparing the composition includes a powdered oil-soak type clay drying agent to the mixture to maintain the mixture in a dry, fine, flowable powder. This composition is not believed to be quickly rainproof nor economical to broadcast. The composition is not believed to promote replacement plant growth to help break up the fire ant mound to thereby prevent reinfestations.

U.S. Pat. No. 6,153,181 issued to Nelson et al. on Nov. 28, 2000, discloses a granular pest bait. A substantially water-free insecticidal granular bait suitable for controlling crawling insects such as cockroaches and ants. The bait includes an insecticide, several feeding stimulants which are typically carbohydrates and proteins, and a lipid. These bait compositions are in granular form, which are useful for application in hard-to-reach areas and are particularly useful in wet conditions, as well as hot, dry areas. This composition is not believed to be economical to broadcast. The composition is not believed to promote replacement plant growth to help break up the fire ant mound to thereby prevent reinfestations.

U.S. Pat. No. 5,618,565 issued to Thomas on Apr. 8, 1997, discloses a composition for exterminating fire ants. A dry powder composition of matter which consists essentially of sodium bicarbonate, a powdered acid, an ant attractant, and a deterrent for animals, birds and insects other than fire ants, such as red chili powder or capsaicin, has been found to selectively kill fire ants, once eaten by the ants or taken into a warm, moist ant mound. The composition does not harm humans, cattle, horses, birds, rodents, etc., and also will not harm black, red, or sugar ants. This composition is not believed to be quickly rainproof nor economical to broadcast. The composition is not believed to promote replacement plant growth to help break up the fire ant mound to thereby prevent reinfestations.

U.S. Pat. No. 5,679,365 issued to Henderson et al. on Oct. 21, 1997, discloses a composition and method for forming an insecticide. A method for preparing and a product made thereby for a bait insecticide composition that is toxic toward fire ants (Solenopsis saevissima v. richterii). Such a composition is comprised of an attractant agent (concord grape extract) mixed with a toxicant (organophosphorous compound) and an enhancing agent (salt). This present invention has the ability to control fire ants while remaining environmentally safe by being inert with regard to most other ants and nearly all other types of insects, rodents and mammals. This material is normally a liquid or gel that can be difficult to apply and/or broadcast across large areas. This composition is not believed to be quickly rainproof. The composition is not believed to promote replacement plant growth to help break up the fire ant mound to thereby prevent reinfestations.

U.S. Pat. No. 6,831,104 issued to Taylor on Dec. 14, 2004 discloses an insect pest eradication system. An insect pest eradication system comprised of a non-lethal knockout agent and an insecticide. The present invention also relates to a method of eradicating insects, particularly those found in earthen colonies, by treating the insects with a non-lethal knockout agent, such as trans-dichloroethylene, in combination with a suitable insecticide for the targeted insects. This composition is not believed to be quickly rainproof nor economical to broadcast. The composition is not believed to promote replacement plant growth to help break up the fire ant mound to thereby prevent reinfestations.

U.S. Pat. No. 4,320,130 issued to Balsley et al. on Mar. 16, 1982 discloses a bait compositions for the control of insects prepared from pregel corn and a toxicant. There is provided a pesticidal bait composition useful for the control of insects, such as fire ants. There is also provided a method of preparation of said baits, whereby pregel defatted corn grits are blended with a solution of a toxicant in a mixture of an edible oil, such as soyabean oil, and a higher fatty acid, such as oleic or stearic acid. This composition is not believed to be quickly rainproof nor economical to broadcast. The composition is not believed to promote replacement plant growth to help break up the fire ant mound to thereby prevent reinfestations.

U.S. Pat. No. 6,916,469 issued to Rojas et al. on Jul. 12, 2005 discloses a gellable ant bait matrix. Ant foods mixed together in a matrix suitable to be used as baits for ants are provided. This ant matrix is preferred by ants over naturally-occurring foods such as other known ant matrices. It comprises protein, carbohydrate, fat and sterol as ant-preferred nutrients and uric acid as a bait enhancing agent is carried in a unique gel system that is specifically attractive to insects. Methods of controlling ants using such matrices to deliver ant toxins are also provided. This composition is not believed to be quickly rainproof nor economical to broadcast. The composition is not believed to promote replacement plant growth to help break up the fire ant mound to thereby prevent reinfestations.

U.S. Pat. No. 5,939,061 issued to Vail et al. on Aug. 17, 1999, discloses an ant bait attractive to multiple species of ants. An attractant composition has been discovered for the control of multiple species of pest arthropods, particularly multiple species of pest ants. The composition, which includes a sugar and a salt or base, and water, attracts both oil-loving and sweet-loving ants and is especially useful with water soluble or suspendable toxicants. This composition is not believed to be quickly rainproof nor economical to broadcast. The composition is not believed to promote replacement plant growth to help break up the fire ant mound to thereby prevent reinfestations.

U.S. Pat. No. 4,874,611 issued to Wilson, et al. discloses a method of manufacture and composition of a core including an insect poison encapsulated in a shell material. The shell was resistant to water but could be penetrated by some insects. It is believed that fire ants often have trouble penetrating the shell and that this method is not very successful in causing the termination of large numbers of fire ants. This composition is not believed to be quickly rainproof nor economical to broadcast. The composition is not believed to promote replacement plant growth to help break up the fire ant mound to thereby prevent reinfestations.

U.S. Pat. No. 3,962,461 issued to Brown, Jr., et al. discloses a toxic bait for insects, in which the bait contains suspended recrystallized Mirex in a sweet, aqueous solution. This substance is used to combat carpenter ants and is not specifically designed to attract fire ants. Since fire ants differ greatly in appetite and in other ways from carpenter ants, it is believed that fire ants have not been greatly attracted to this bait, resulting in an ineffective insecticide for fire ant application. This composition is not believed to be quickly rainproof nor economical to broadcast. The composition is not believed to promote replacement plant growth to help break up the fire ant mound to thereby prevent reinfestations.

U.S. Pat. Nos. 4,460,606 and 4,540,711 both issued to Bettarini, et al. disclose a method for fighting infestation by fire ants consisting of a bait comprising hydroquinone diether having at least one acetylenic and halogen-substituted chain and selected from 1-[(5-chloro-pent-4-inyl)-oxy]-4 phenoxybenzene and 1,4-di-(5-chloro-4-pentinyloxy)-benzene. Like the Brown pesticide, it is believed that the Bettarini disclosure has not been successful in reducing fire ant infestations significantly. This composition is not believed to be quickly rainproof nor economical to broadcast. The composition is not believed to promote replacement plant growth to help break up the fire ant mound to thereby prevent reinfestations.

U.S. Pat. No. 3,220,921 issued to Greenbaum, et al. discloses a poison containing a bait composition. This composition eliminates fire ants but it also attracts many beneficial insects (i.e., bees, flies, beetles, etc.). Therefore, this bait has the disadvantages of attracting insects that should not be extinguished because it will upset the ecological balance and eliminates insects, such as honey bees, which are commercially and environmentally desirable. Furthermore, although this bait attracts fire ants, it does not appear to attract them to the degree necessary to rid large areas of fire ants. Lastly, there appears to be problems with the form of this composition (primarily solid), which makes it difficult to distribute in large quantities over a large geographical area. This composition is not believed to be quickly rainproof nor economical to broadcast. The composition is not believed to promote replacement plant growth to help break up the fire ant mound to thereby prevent reinfestations.

U.S. Pat. Nos. 5,094,853, 5,104,658 and 5,116,618 issued to Hagarty disclose a killing composition containing an organophosphorous compound mixed with a corn sweetener. These compositions by Hagarty are pesticides in the form of arthropodicidally-active foam matrices. Like the Greenbaum '921 patent composition, this insecticide was designed to control fire ants, as well as certain crustaceans, arachnids, a wide variety of crawling insects and certain myriapods. The problem with this composition, once again, is that it attacks more insects than simply fire ants. Therefore, it too appears to upset the ecological balance more than necessary and it kills desirable insects. This composition is not believed to be quickly rainproof nor economical to broadcast. The composition is not believed to promote replacement plant growth to help break up the fire ant mound to thereby prevent reinfestations.

Unlike the present invention, the known art toxic compositions are consumed by a variety of species and, thus, most cannot be used under circumstances where it is necessary for insects and other species to thrive. Thus, there exists a need in the field of fire ant control, as well as the zoological field, for improved technology relating to controlling and/or eradicating fire ant infestations safely and in an ecologically sound fashion. In particular, there is a need to improve the desirable attributes of fire ant baits and pesticides while simultaneously maintaining the expected performance characteristics of the pesticide and especially the ability to broadcast the bait over a target mound to ensure it is taken by the ants into the nest.

SUMMARY OF THE INVENTION

The invention provides for an improved fire ant pesticide and/or bait. The present invention provides a fire ant pesticide composition and method that is normally in the form of a dust or powder or even wettable powder. This composition is comprised of a plurality of insect attractants, at least one plant growth stimulator, a plurality of insectides, of which all but one are organic, and various other components to improve the stability and flowability of the composition. The primary purpose of the present composition is to eradicate fire ants infestations in a most environmentally friendly way, while also preventing subsequent reinfestions of the same mound along with the physical destruction of the empty mound. The production costs involved in this invention are believed to be highly competitive with other formulas available in the market place.

The insect attractant for the present invention can be chosen from numerous components so long as they are generally safe for human and animal consumption. In particular various types of fruit gelatin mixes have been demonstrated to work acceptably in one embodiment in accordance with the present invention. In addition to the gelatin mix, generic super fine granulated sugar and blood meal are also used to attract ants as well as to enhance the stickiness of the resultant composition. In addition to the insect attractants, other components such as self rising white corn meal, fresh water food grade diatomaceous earth and a specialized preparation of tortilla flour may be used to promote the flowability and stability of the composition. The corn meal and tortilla flour are both palatable foodstuffs and are believed detrimental to the ants' digestive systems. The fresh water food grade diatomaceous earth is a known pesticide to exoskeletal insects, acting to lacerate their hard outer shells, then acting as an absorbent to bodily fluids, resulting in death. The plant growth stimulator is preferably nitrogen based and blood meal is suitable.

Thus, the composition includes the following components. White self rising corn meal is a component, which has shown itself to be a very effective appetite attractant to fire ants. Our experiments have illustrated that (having used both ingredients) the self-rising meal is a more effective lure for these insects than plain corn meal and, quite possibly, may even be a destructive agent when introduced into the fire ant's digestive system, causing internal bloating of the digestive tract. This added benefit of the self-rising type meal may be the result of its combination with other formula ingredients or it might be a digestive blocker in and of itself, thereafter resulting in the insects' death.

Fresh water food grade diatomaceous earth (hereinafter sometimes abbrev. "DE") is a natural product that is available in two forms: "Salt Water, Non Food Grade" and "Fresh Water, Food Grade". The latter is a very safe substance which is environmentally friendly and found in nature. This latter grade of DE is also well recommended for the control of pests such as fleas, cockroaches and many other insects when used as an external treatment in the coats of pets, in home interiors and in other environs where pesticides are less than the best choice of treatment. Diatomaceous Earth though, is a fatal substance to many insects such as fire ants because, once exposed to these types of exoskeleton insects, the razor sharp nature of DE (on such a small scale dimension) lacerates the external skeleton of the insect and the absorbent nature of DE then dehydrates the pest quickly, resulting in its death. Another advantage of incorporating this grade of DE into our formula is its very favorable volume to weight ratio, which results in a greater bulk of product to the end user for each pound of product purchased. DE is a substance that is relatively light in weight and therefore provides the end user with more bulk material per pound purchased than most other fire ant control agents. In quantity, this ingredient offers very high efficacy as an admixture to the formula, serving both as an effective organic pesticide and as a low cost bulk additive that gives greater coverage per ounce of material applied to each colony. Fire ants need not ingest DE for it to be an effective killer. Once these insects are externally exposed to this natural product, the DE residue immediately begins working to kill the ant by incising their hard shell skeleton and then dehydrating their bodily fluids. Because of its extremely fine physical properties through, one should expect some amount of product consumption by the insects, resulting in ingestion damages as well as external effects. The inclusion of DE is further enhanced by the fact that this purely organic substance is a product that does not require safety precautions at neither the mining and transport nor at the end user level for other than targeted insects. One should only take the normal precautions to avoid breathing in larger quantities of DE, just as the individual would avoid doing the same in a sandstorm (for instance). There is no recognized need to avoid normal exposure to the Fresh Water, Food Grade type of DE. It is, in fact, a beneficial diet supplement for most. The diatoms that compose this product are microscopically tiny and are razor sharp but they have no detrimental effect on other than hard shell insects such as small ants. Quite the contrary, on larger animals their shells have an internal cleansing effect.

Ruminant blood meal is a product of the slaughterhouse, just as are most of the commercially available meats and their byproducts commonly purchased from grocery cases and consumed by families worldwide. "Ruminant" is a descriptive term indicating that this meal is a byproduct of cud chewing animals such as cattle and sheep. Blood meal is a palatable and attractive substance to carnivores such as fire ants. It is harmless, though less than palatable, to humans and most other animals. Blood meal is also a valuable organic fertilizer, long recognized as a plant stimulant by gardeners and it is considered to be a soil enhancing agent of some excellence. Blood meal is strictly non-toxic and is non-chemical in origin. Blood meal acts as an ant attractant in this formula and it enhances the ingestion of other ingredients that are a part of the mixture which serve as killing agents in the ant colony.

Generic brand cherry flavor gelatin dessert mix serves as a flavored sweetener attractant that promotes the ingestion of the formulas various other ingredients, among which are the agents that kill the targeted ant population. Various gelatins have been tried in our experiments. Fire ants appear to have a preference for this particular flavor, as a favorite choice fit with the other ingredients in our product. Naturally, this gelatin mix is harmless to the environment and to animals and plants, generally. It is strictly a non-harmful attractant to the ant bait.

Generic brand super fine granulated sugar has performed well in our experiments although various types of powdered and granulated sugars have also worked, all serving to one degree or another satisfactorily. The preferred ingredient in this class of attractants for our purposes has been this specific type of sugar. It is a granular, rather than a powdered sugar, yet it is of a fine consistency that lends itself nicely to apparent ease of ingestion by the small targeted insects. When in the final mixture, this fine grade of sweetener is generally indistinguishable from the various other ingredients insofar as its size, even when viewed microscopically. As a fine granular substance, it does not seem to have the undesirable tendency of promoting clumping of the final product.

Harina Preparada (aka masa white flour tortilla mix) is a particularly palatable appetite attractant for fire ants that is manufactured by several distributors and serves to enhance ingestion of the entire formula, including the pesticides intended to eliminate the fire ant colony. There are only very minor differences between one brand of this product and competing brands. The example referenced herein in supplied by the Quaker Oats Company of Chicago and the list of its ingredients, in a typical four pound package, are as follows:

| | |
|---|---|
| Total fat: | 7% |
| Sodium: | 17% |
| Carbohydrates: | 9% |
| Dietary Fibers: | 4% |
| Calcium: | 6% |
| Thiamin: | 15% |
| Niacin: | 10% |
| Iron: | 10% |
| Riboflavin: | 10% |
| Folic Acid: | 10% |

Fractional additives of sugar and protein round out the total to 100%.

Substantially pure acephate (commonly accepted as at least 97% active ingredient) is the primary chemical toxicant. Our product formula utilizes less than 4% pure acephate (by weight) in its formula as one of at least two (possibly three) ant killing agents (the others being DE and, probably, self rising corn meal). This mixture of acephate is among the lowest chemical percentages of any fire ant product on the market, yet our formula has been demonstrated to be more highly effective, environmentally friendly and demonstrably cost effective when compared to most or all other competing products.

The acephate, an organophosphorous compound, is added in small quantities to this mixture to make the composition most toxic to fire ants. For example, a most suitable poison is acetylphosphoramidothiotic acid O, S-dimethyl ester, more commonly called "Acephate," and commercially available from many companies (See also U.S. Pat. Nos. 3,716,600 and 3,845,172, both assigned to Chevron); however, the percentage of toxicity in this formula is exceptionally low when compared to other available effective treatments.

As mentioned previously, one problem that can be encountered when eradicating fire ants is that they sometimes repopulate old mounds or nests. The present invention has a relatively long period of effectiveness and it continues to kill new inhabitants of the old nests for many weeks and even months after treatment. Thus, contrary to the several other more toxic compositions, this composition rids both current and possibly future re-generations of fire ants. Moreover, the plant growth stimulator of the present invention also promotes the natural destruction of the fire ant mound as a result of new plant life after the current colony is eradicated.

A basic object of the present invention is to provide an improved fire ant pesticide that is relatively safe while being highly effective at eliminating fire ant infestations.

An object of the present invention is to provide a composition that is quickly rainproof so that subsequent unintended wettings do not adversely affect the pesticidal efficacy of the composition.

Yet another object of the present invention is to provide a composition that resists clumping when exposed to high humidity conditions.

An object of the present invention is to provide a composition that may be economically spread by broadcasting it around and about the targeted fire ant mound.

Another basic object of the present invention is to provide a pesticide that promotes intentional replacement plant growth to break up the fire ant mound.

Another basic object of the present invention is to provide a pesticide that does not generate offensive odors when applied.

An object of the present invention is to provide a pesticide that eliminates fire ant colonies absent the frequently experienced satellite colony regeneration(s), commonly associated with many other pesticides. The Texas A&M test results of this product directly addressed many of the listed objectives outlined above.

These and other objects and advantages of the present invention, along with features of novelty appurtenant thereto, will appear or become apparent by reviewing the following detailed description of the invention.

BRIEF DESCRIPTION OF THE SEVERAL VIEWS OF THE DRAWINGS

In the following drawings that form a part of the specification which are to be interpreted in conjunction therewith, and in which reference numerals have been employed when possible to indicate like parts in the various views:

FIG. 1, FIG. 2, FIG. 3 and FIG. 4 are photographs showing a fire ant mount (measuring approximately 32"×18") in the treatment process in accordance with the present invention.

FIG. 5, FIG. 6 and FIG. 7 are photographs showing the same fire ant mound approximately 72 hours after treatment in accordance with the present invention.

DETAILED DESCRIPTION OF THE INVENTION

Figure 1:
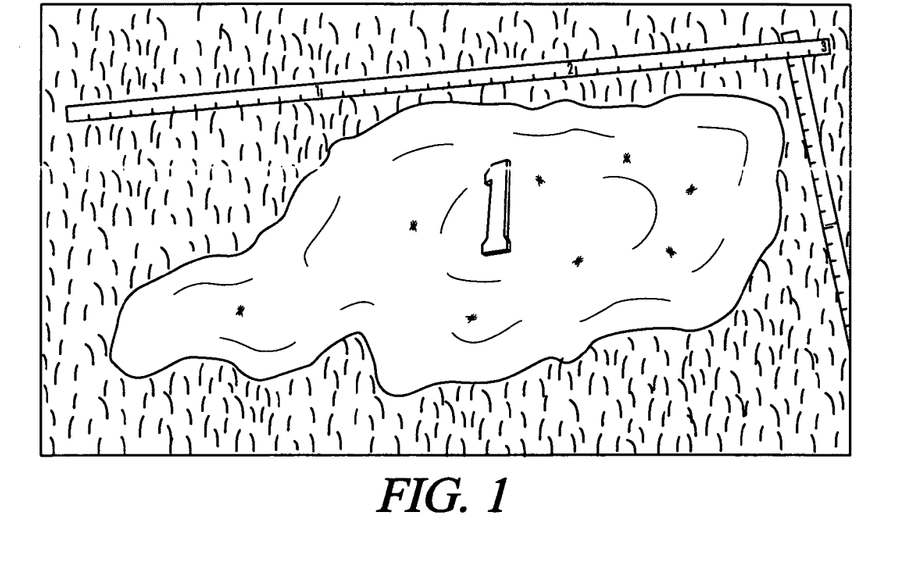
FIG. 1 is a photograph displaying fire ant mound (measuring approximately 32"×18") prior to disturbance and treatment.
Figure 2:
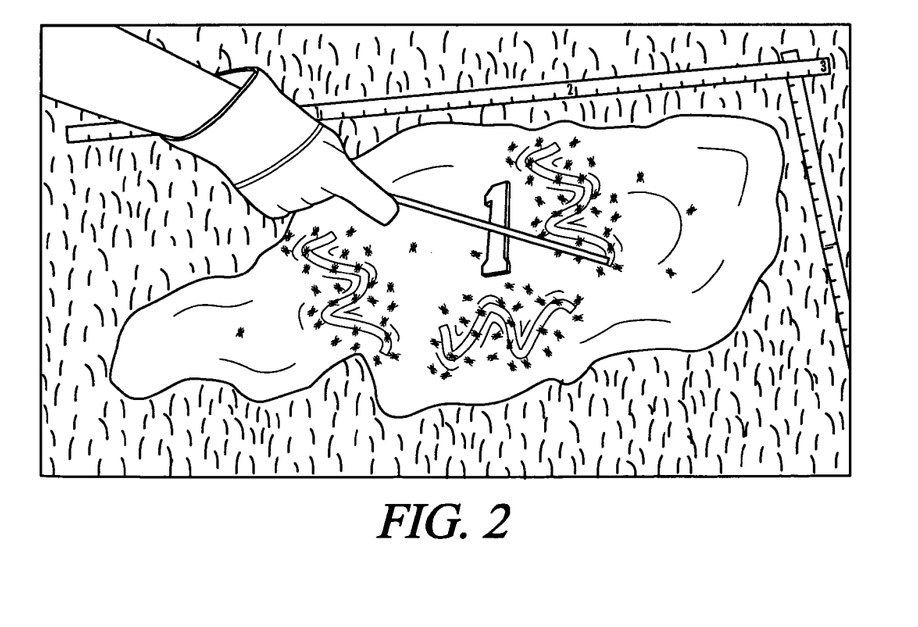
FIG. 2 is a photograph displaying the same fire ant mound as represented in FIG. 1, being agitated on its surface by a wire device.
Figure 3:
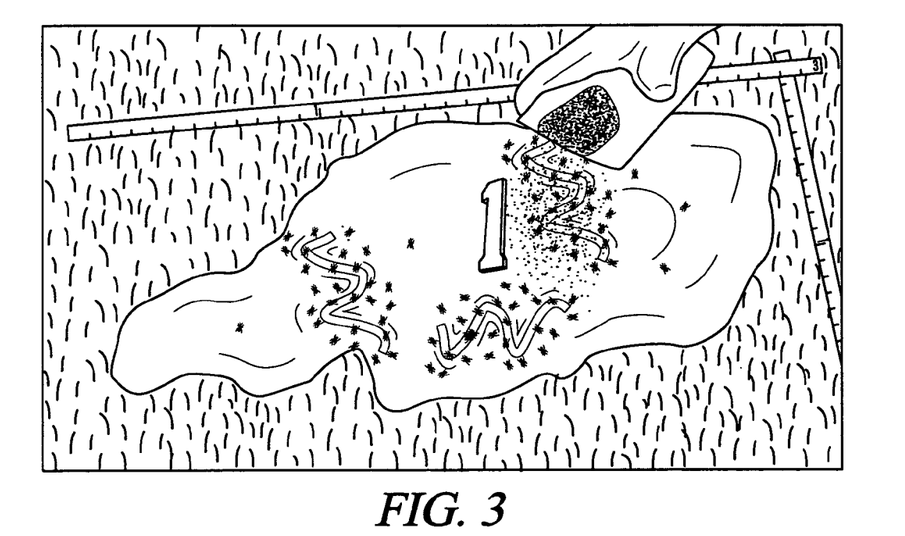
FIG. 3 is a photograph displaying the same fire ant mound as represented in FIG. 1, with product being spread on fire ant mound.
Figure 4:
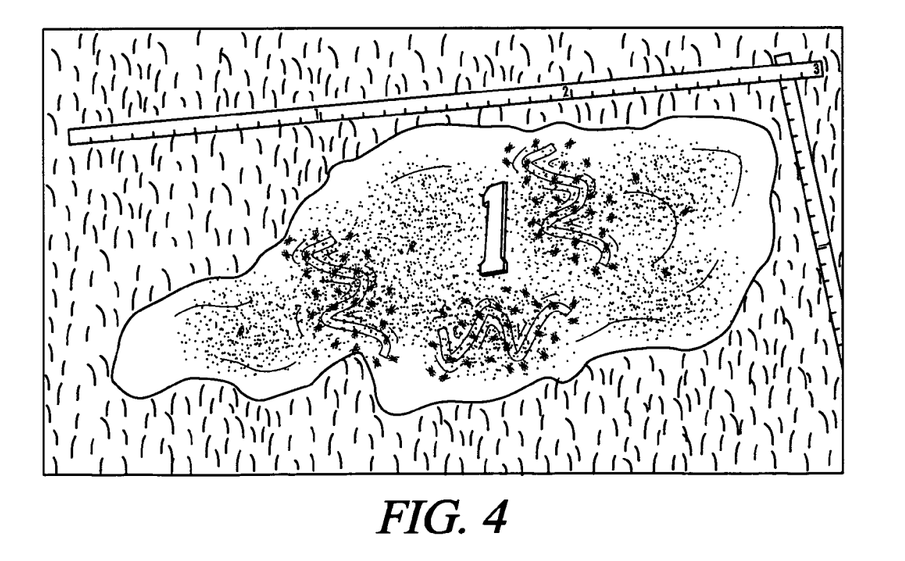
FIG. 4 is a photograph displaying the same fire ant mound as represented in FIG. 1, immediately after treatment.
Figure 5:
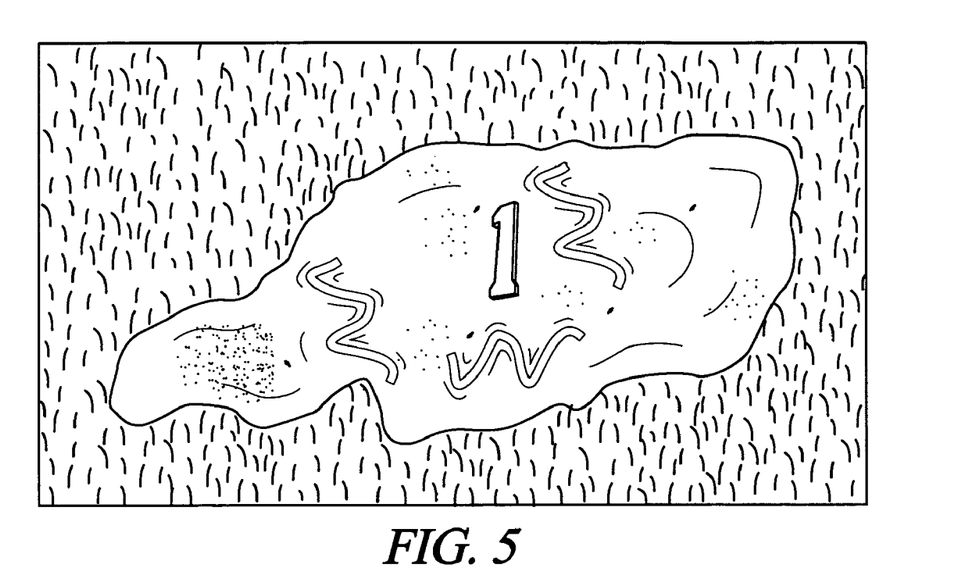
FIG. 5 is a photograph displaying the same fire ant mound as represented in FIG. 1, 72 hours post-treatment. Please note the diminution of product.
Figure 6:
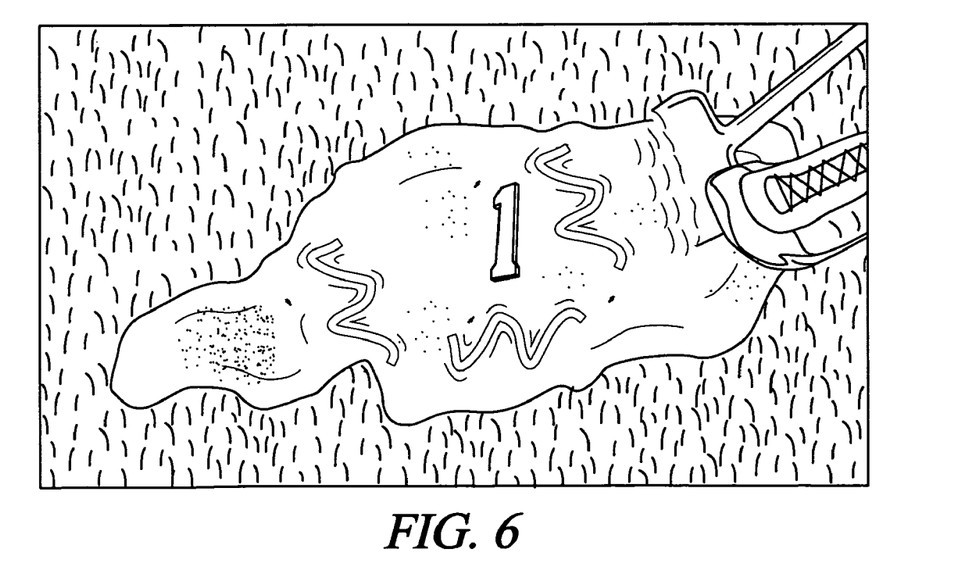
FIG. 6 is a photograph displaying the same fire ant mound as represented in FIG. 1, fire ant mound being investigated 72 hours post-treatment. Investigation is performed by digging up fire ant mound with use of shovel.
Figure 7:
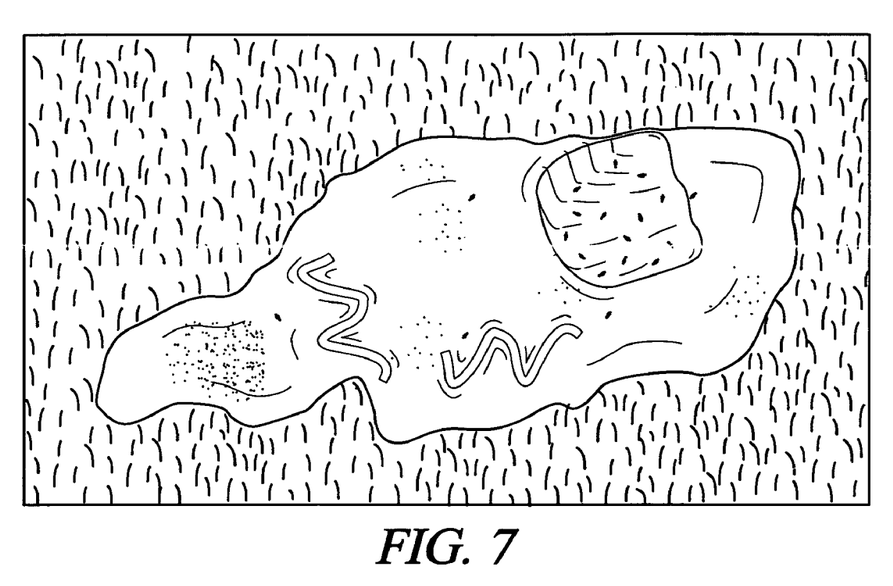
FIG. 7 is a photograph displaying the same fire ant mound as represented in FIG. 1, fire ant 72 hours post-treatment with mound being dug up. No live ants were apparent in this colony.

In accordance with the present invention, a pesticide is formed that can be used to eradicate fire ants and promote subsequent mound destruction. This invention comprises a formula including several components that attract fire ants, a plant growth stimulator, and a plurality of insecticides (at least two insecticides and perhaps three: Acephate, Diatomaceous Earth and possibly, but not certainly, self rising flour) and other components to preserve the composition and its stability and flowability.

The invention provides for an improved and highly effective fire ant pesticide and/or bait. The present invention provides a fire ant pesticide composition and method therefore, that is normally in the form of a dust or powder or even wettable powder. This composition is comprised of at least one insect attractant and preferably several, at least one plant growth stimulator, at least one insectide and various other components to improve the stability and flowability of the composition. The primary purpose of the present composition is to eradicate fire ants infestations while, concurrently, providing a very, high degree of environmental awareness. The present invention has also shown itself to prevent subsequent re-infestations of the same mound. The present invention also promotes the physical destruction of the empty mound.

The insect attractants for the present invention can be chosen from numerous components so long as they are generally safe for human and animal consumption. Various types of fruit gelatin mixes should work acceptably in the present invention but one type of cherry gelatin mix has been demonstrated to work very well in accordance with the present invention. The known fruit gelatin mix that works well with the present invention is a generic cherry gelatin dessert mix (which includes cherry flavoring and other ingredients) but other cherry gelatin dessert mixes such as those sold under the commercial brand name Jell-O® will also sufficiently work. While many ingredients could be used with the present invention, the primary requirement for the insect attractant is that the fire ants eat and/or transport the composition back into their mound. The composition includes at least one suitable attractant and preferably cherry gelatin dessert mix at a concentration of between 2 percent and 10 percent of total formula weight. Other types of gelatin mixes may be substituted so long as fire ants are attracted to the resulting composition.

In addition to the gelatin mix, generic brand granulated superfine pure cane sugar is also used to attract ants. This ingredient also enhances stickiness of the resultant composition. This attractant is included in the composition at a concentration between approximately 2 percent and approximately 12 percent, by weight of the total formula. Other types of granulated sugars including brown, powdered, and the like may be substituted so long as fire ants are attracted to the resulting composition.

Other ingredients used in one embodiment of the present invention include several that function as attractants but that also add other desirable traits to the overall composition. In addition to the fruit gelatin mix and sugar, generic self rising white corn meal is used to attract fire ants as well as promote the flow-ability and act as a carrier in the composition. A number of previous studies have indicated that, once ingested, self rising corn meal is highly detrimental to the digestive system of fire ants and may contribute to their eradication. Self rising white corn meal is included in the formula at a concentration between approximately 29 percent and approximately 39 percent, by weight of the composition. In addition to corn meal, generic white flour tortilla mix (which includes white flour and various other ingredients) is commonly sold under the brand name(s) of HARINA PREPARADA and others. These are also included to attract ants as well as to promote the flowability and to preserve the composition. The tortilla mix is included in the formula at a concentration between approximately 2 percent and approximately 8 percent, by weight of the composition. Fresh water, food grade Diatomaceous Earth is used to stabilize the composition, provide an additional important pesticide and to promote flowability of the product as well. Diatomaceous earth is included in the composition at a concentration between approximately 15 percent and approximately 25 percent, by weight of the composition.

In accordance with one embodiment of the present invention, a plant growth stimulator is also included in the formula to encourage plant growth throughout the eradicated fire ant mound. The preferred plant growth stimulator and preferably ruminant blood meal at a concentration between approximately 22 percent and approximately 32 percent, by weight of the composition. Ruminant blood meal is incorporated into the formula for the purposes of serving as an ant attractant and, thereafter, as an organic fertilizer that encourages rapid growth of root systems into the soil after elimination of the ant colony. Blood meal is dried, powdered blood often used as a high-nitrogen fertilizer. It is one of the highest non-synthetic sources of nitrogen, though if over-applied it can burn plants with excessive ammonia. Blood meal is completely soluble and can be mixed with water to be used as a liquid fertilizer. It usually comes from cattle, sheep or other livestock as a slaughterhouse by-product. As with other products in this formula, it is a harmless, although unpalatable, ingredient to humans, animals and most living creatures excepting those insects intended for eradication via admixture solutions.

The composition includes an insecticide and preferably an organophosphorous compound at a concentration between approximately 1 percent and approximately 4 percent, by total weight of the composition. For purposes of the present invention, suitable organophosphorous compounds include phosphates, phosphoronionates, and phosphorothionates. For example, suitable, well-known organophosphorous compounds, useful as insecticides in the present invention includes acetylphosphoramidithiotic acid O,S-dimethyl ester, more commonly called "Acephate," and commonly is commercially available from a variety of sources.

Other examples of suitable organophosphorous compounds which have toxic effects for fire ants, include, but are not limited to, phosphorothioic acid O,O-diethyl O-(3,5,6-trichloro-2-pyridinyl) ester, also known by "Chlorpyrifos", and commercially available under the "Dursban", "Lorsban", and "Pyrinex" brand names (see also U.S. Pat. No. 3,244,586 assigned to Dow Chemical); phosphorothioic acid O,O-diethyl O-[6-methyl-2-(1-methylethyl)-4-pyrimidinyl]ester, also known by "Dimpylate", and commercially available under the "Basudin", Diazinon", "Diazol", "Garden Tox", "Sarolex", and "Spectracide" brand names (see also U.S. Pat. No. 2,754,243 assigned to Geigy); phosphorothioic acid O,O-dimethyl O-(3-methyl-4-nitrophenyl) ester, also known by "Fenitrothion", and commercially available under the "Accothion", "Cyfen", Cyten", "Folithion", "MEP", "Metathion" and "Sumithion" brand names (see also Belgian Patent No. 594,669 to Sumitomo as well as Belgian Patent No. 596,091 to Bayer); phosphorothioic acid O,O-dimethyl O-[3-methyl-4-(methylthio)phenyl]ester, also known by "Fenthion", and commercially available under the "Baycid", "Baytex", "Entex", "Lebaycid", "Mercaptophos", "Queletox", "Spotton", "Talodex" and "Tiguvon" brand names (see also German Patent No. 1,116,656 as well as U.S. Pat. No. 3,042,703, both assigned to Bayer; see also Japanese Patent No. 15,130, which issued in 1964 to Sumitomo); 4-ethoxy-7-phenyl-3,5-dioxa-6-aza-4-phosphaoct-6-ene-8-nitrile 4-sulfide, also known by "Phoxim", and commercially available under the "Baythion", "Sebacil" and "Volaton" brand names (see also U.S. Pat. No. 3,591,662 assigned to Bayer); and the O,O-dimethyl analog of O-[2-(diethylamino)-6-methyl-4-pyrimidinyl]phosphorothioic acid O,O-diethyl ester, also known by "Pirimiphos-methyl", and commercially available under the "Actellic", "Blex", and "Silo San" brand names. (See, e.g., entry numbers 25, 2167, 2968, 3910, 3927, 7251 and 7372, respectively, in "The Merck Index", 10th ed., published in 1983 by Merck & Co., Inc.).

As mentioned previously, one problem sometimes encountered when eradicating fire ants is that they repopulate old mounds or nests. The present invention has a relatively long period of toxicity and it continues to kill new inhabitants of the old nests for many weeks and even months after treatment. Thus, contrary to the several other toxic compositions, the composition rids both the present and potential replacement generations of fire ants. Moreover, the plant growth stimulator in the present invention also promotes the natural destruction of the fire ant mound as a result of plants growing through and into the mound after the ants cease maintenance thereof.

Thus, the present invention provides an improved fire ant pesticide that is relatively safe while being very effective at eliminating fire ant infestations. The present invention also provides a composition that is quickly rainproof so that subsequent wettings do not adversely affect the pesticidal efficacy of the composition. Experiments with this product have shown a reliable tendency for elimination of the treated fire ant colonies even occurring at an accelerated rate when light to moderate rainfall occurs within the first twelve hours of product application onto dry ground. The present invention provides a composition that resists clumping when exposed to high humidity conditions and that may be economically spread by broadcasting it directly upon and around the fire ant mound to be eradicated, when applied according to tested conditions.

The present invention will hereunder be described in even greater detail by reference to the following Examples, which are given here for illustrative purposes only and are by no means intended to limit the scope of the present invention.

Mixture 1/Test 1

A mixture was prepared according to the following formula:

| Ingredient | weight (oz) | weight % |
| --- | --- | --- |
| Corn Meal | 45 to 50 | 33% to 36% |
| Diatomaceous Earth | 35 to 40 | 26% to 28% |
| Blood Meal | 35 to 40 | 26% to 28% |
| Gelatin Mix | 2 to 5 | 2% to 3% |
| Sugar | 3 to 6 | 2% to 3% |
| Acephate | 5 to 10 | 2% to 6% |
| Total | 125 to 151 | |

The acephate and blood meal were finely screen strained into a large container and the remaining ingredients where then added and thoroughly mixed to produce a fine powder with no clumps. A target fire ant mound between 6 to 10 inches in diameter was first irritated by lightly disturbing the top surface of the mound with a small twig or wire in order to prompt an angry, agitated response from the colony. The mixture was then sprinkled on and around the mound. Within 24 hours, fire ant consumption was apparent, particularly after digging into the fire ant mound to examine the internal structure.

Mixture 1/Test 2

A mixture was prepared according to Mixture 1. The mixture was then applied to a target fire ant mound between 6 to 10 inches in diameter after mound disturbance. After approximately 1 hour, a gallon of water was lightly sprinkled across the mound to simulate a light to moderate rainfall. Within 24 hours, the fire ant mound was dissected, finding that fire ant activity still existed. A further examination after 72 hours discovered that fire ant activities remained with ants quite active.

Mixture 2/Test 1

A mixture was prepared according to the following formula:

| Ingredient | Weight (oz) | weight % |
| --- | --- | --- |
| Corn Meal | 35-40 | 30% to 35% |
| Diatomaceous Earth | 25-30 | 22% to 25% |
| Blood Meal | 30-35 | 26% to 30% |
| Gelatin Mix | 2-8 | 2% to 8% |
| Sugar | 2-8 | 2% to 8% |

-continued

| Ingredient | Weight (oz) | weight % |
|---|---|---|
| Tortilla Mix | 3-6 | 3% to 6% |
| Acephate | 4-8 | 4% to 8% |
| Total | 101 to 135 | |

The acephate was screen strained into a large container and the remaining ingredients were then added and thoroughly mixed to produce a fine powder with no clumps. A target fire ant mound between 6 to 10 inches in diameter was first irritated by disturbing the top of the mound and then the mixture was sprinkled on and around the mound. Within 72 hours, visible fire ant activity ceased but through dissection of the mound, it was found that some fire ant activity remained. Fire ants were either killed or those that remained alive exhibited lethargic movements and were not as active as before testing.

Mixture 2/Test 2

A mixture was prepared according to Mixture 2. The mixture was then applied to a target fire ant mound between 6 to 10 inches in diameter following mound disturbance. After approximately 1 hour, a gallon of water was lightly sprinkled across the mound to simulate a light to moderate rainfall. Within 24 hours, most fire ant activity ceased. The mound was dissected and ants either were killed or those surviving showed very lethargic movements.

Mixture 2/Test 3

A mixture was prepared according to Mixture 2. The mixture was then applied to a target fire ant mound between 24 and 30 inches in diameter after mound disturbance. Within 72 hours, visible fire ant activity ceased but through dissection of the mound, it was found that fire ant activity still remained. Fire ants were either killed or those that remained alive showed very lethargic movements and were obviously not as active as before testing.

Mixture 2/Test 4

A mixture was prepared according to Mixture 2. The mixture was then applied to a target fire ant mound between 24 and 30 inches in diameter after mound disturbance. After approximately 1 hour, a gallon of water was lightly sprinkled across the mound to simulate light to moderate rainfall. Within 24 hours, almost all fire ant activity ceased. The mound was dissected and ants either were killed or those surviving, showed very lethargic movements.

Mixture 3/Test 1

A mixture was prepared according to the following formula:

| Ingredient | weight (oz) | weight % |
|---|---|---|
| Corn Meal | 36 to 49 | 29% to 39% |
| Diatomaceous Earth | 19 to 31 | 15% to 25% |
| Sugar | 3 to 15 | 2% to 12% |
| Gelatin Mix | 3 to 15 | 2% to 12% |
| Tortilla Mix | 3 to 10 | 2% to 8% |
| Blood Meal | 27 to 40 | 22% to 32% |
| Acephate (97% pure) | 1 to 5 | 1% to 4% |
| Total | 125.5 | 100% |

Total weight is equivalent to 7.84375 pounds

The acephate was screen strained into a large container and the remaining ingredients where then added and then thoroughly mixed to produce a fine powder with no clumps. A target fire ant mound between 6 to 10 inches in diameter was first irritated by disturbing the top of the mound and then the mixture was sprinkled on and around the mound. Within 72 hours, visible fire ant activity ceased. The mound was dissected by digging into the mound to examine the internal structure. Dissection of the mound revealed only dead fire ants; no surviving fire ants and thus complete morbidity was demonstrated. In checking the mounds (over the course at schedules of one, two, three and four weeks after application) it was found that no satellite mounds appeared within a nearby distance of the originally treated mound. No re-emergence of the colony was evident. Checks were made at sixty, ninety and one hundred twenty days on this and other similarly treated fire ant mounds. No evidence of re-population was apparent.

Mixture 3/Test 2

A mixture was prepared according to Mixture 3. The mixture was then applied to a target fire ant mound between 6 to 10 inches in diameter following mound disturbance. After approximately 1 hour, a gallon of water was lightly sprinkled across the mound to simulate light to moderate rainfall. Within 36 hours, all visible fire ant activity ceased. The mound was dissected and no surviving fire ants were found. Dissection of the mound revealed only dead fire ants; no surviving fire ants and thus complete morbidity was demonstrated. In checking the mounds (over the same preceding time periods as outlined in Mixture 3/Test 1), it was found that no satellite mounds appeared within a nearby distance of originally treated mound. No evidence of any re-population existed.

Mixture 3/Test 3

A mixture was prepared according to Mixture 3. The mixture was then applied to a target fire ant mound between 24 and 30 inches in diameter following mound disturbance. Within 72 hours, all visible fire ant activity ceased. The mound was dissected and no surviving fire ants were found. Dissection of the mound revealed dead fire ants, no surviving fire ants and thus complete morbidity was established. In checking the mounds (over the course of following 30 days), it was found that no satellite mounds appeared within a nearby distance of originally treated mound. The same schedule of analysis as previously reviewed (with Mixture 3) was applied, with same results.

Mixture 3/Test 4

A mixture was prepared according to Mixture 3. The mixture was then applied to a target fire ant mound between 24 and 30 inches in diameter following mound disturbance. After approximately 1 hour, a gallon of water was similarly sprinkled across the mound to simulate light to moderate rainfall. Within 72 hours, all visible fire ant activity ceased. The mound was dissected and no surviving fire ants were found. Dissection of the mound revealed dead fire ants, no surviving fire ants and thus complete morbidity was established. In checking the mounds (over the course of following 30 days), it was found that no satellite mounds appeared within a nearby distance of originally treated mound. The preceding time analysis and methods were used to verify results. No differences were noted.

The invention has been described with reference to various specific and preferred embodiments and techniques. It will be understood, however, that reasonable modifications of such embodiments and techniques may be made while remaining within the spirit and scope of the invention.

From the foregoing, it will be seen that this invention is well adapted to obtain all the ends and objects herein set forth, together with other advantages which are inherent to the formula structure. It will also be understood that certain features and subcombinations are of utility and may be employed without reference to other features and subcombinations. This is contemplated by and is within the scope of the claims. Many possible embodiments may be made of the invention without departing from the scope thereof. Therefore, it is to be understood that all matter herein set forth or shown in the accompanying drawings is to be interpreted as illustrative and not in any limiting sense.

To substantiate our internal testing's performed on this invention, following is the third-party testing performed by the Texas A&M University AgriLIFE Extension office (late 2007). This evaluative description of testing results is a verbatim report from the Texas A&M Agricultural School, Entomology Department. Within this testing, the invention is referred to as Greene Countrie Enterprise "Fire Ant Hayter Bait".

Evaluation of Greene Countrie Enterprises, LLC "Fire Ant Hayter Bait" for Management of Red Imported Fire Ants Wizzie Brown, Extension Program Specialist, Travis County, Bastiaan M. Drees, Professor and Extension Entomologist, and Alejandro Calixto, Extension Associate Texas Cooperative Extension, The Texas A&M University System Red imported fire ants, *Solenopsis invicta* Buren, are a major problem in the southeastern United States. There are a variety of fire ant control options with common choices being the application of individual mound treatments (granulars, dusts, liquid drenches, aerosol injections, baits), broadcast baits, broadcast granular products, or a combination of aforementioned treatments. Individual mound treatments are often used when there are a small number of fire ants mounds located within a particular area or when mounds appear between broadcast baiting periods. In the "Texas Two Step" approach, individual mound treatment use is reserved for treating only ant colonies that are a nuisance or remain following application of a broadcast-applied bait product. This trial was to test a new individual mound treatment formulation for management of red imported fire ants.

Materials & Methods

This trial was established Oct. 2, 2007, at Riverside Campus of Texas A&M University (Bryan, Tex.). The day was sunny with a slight breeze and temperatures were around 78° F. Twelve plots, each containing 6 active red imported fire ant mounds but varying in size, were established with 10 foot buffers between plots to reduce ant colonies migrating between plots. Plot width remained constant, but length varied to obtain 6 active red imported fire ant mounds within the plot. Plots were measured and arrayed from smallest to largest and divided into four replicates (blocks) each containing three treatment plots. Treatments were assigned randomly within each block.

Treatments included:
1. Untreated control or check—no treatment
2. Ortho® Orthene® Fire Ant Killer (standard Orthene® treatment)—50% acephate; 1 tablespoon sprinkled over each mound
3. Greene Countrie Enterprises "Fire Ant Hayter Bait"—4% acephate formulation; 4 tablespoons sprinkled over each mound Prior to treatment, each mound was marked with a field flag for treatment and examined for red imported fire ant activity using the minimal disturbance method whereby a mound is considered to contain an active colony if a dozen or more worker ants emerge en masse following mild disturbance. Plots were evaluated at 3, 7, 14, and 30 days after treatment by checking marked mound ant activity using the method just described. On the last evaluation date, all imported fire ant mounds were counted within each plot to determine if ant colonies had migrated into or out of plots or "shattered" as a result of treatment.

Data were analyzed using Analysis of Variance (ANOVA) and means separated using Duncan's Multiple Range test at $p \leq 0.05$ (SPSS, Windows 14.0).

Results and Discussion

Weather during this trial period was warm and rather dry (Table 1). These conditions apparently resulted in a 30 percent reduction in ant activity in six untreated control mound plots during the 30 day monitoring period (Table 2). However, comparisons between the three treatments in this trial were still possible by comparing insecticide treatments to the untreated control plot mean ant mound numbers.

During all days following treatment, the average (mean) number of active flagged mounds in the Greene Countrie Enterprises "Fire Ant Hayter Bait" and the Ortho® Orthene® plots were significantly lower than the number of active flagged mounds in the untreated control plots (Table 2). At 30 days after treatment, mean active mounds in the Greene Countrie Enterprises "Fire Ant Hayter Bait" plots were significantly different than the check plots, but not significantly less than the number of active ant mounds in the Ortho® Orthene® plots (Table 3).

The dilute acephate formulation in Greene Countrie Enterprises "Fire Ant Hayter Bait" used less active ingredient to treat each ant mound than Ortho® Orthene® (1 tablespoons of Ortho® Orthene® containing 50% acephate used 0.5 tablespoons of acephate per mound, whereas 4 tablespoons of "Fire Ant Hayter Bait" containing 4% acephate used 0.16 tablespoons acephate per mound). Therefore, use of this product would result in lower amounts of active ingredient applied to the environment than use of the 50% acephate formulation—while achieving similar levels of control. Inert ingredients in the Greene Countrie Enterprises "Fire Ant Hayter Bait" formulation were undisclosed and retail cost of this formulation has not been determined. Thus, product cost comparisons cannot be made at this time.

TABLE 1

Weather data for October 2007 near the Texas A&M University Riverside Campus from Weather Underground (Easterwood Airport), Brazos Co., TX.

| Date | Total Rainfall (inches) | Mean Temperature (F.) |
|---|---|---|
| October 2007 | 2.68 (4.22 is normal) | 72 |

TABLE 2

Mean number of active marked imported fire ant mounds or 10 mounds treated, October 2, 2007, Brazos County, TX.

| | Mean no. Active Ant Mounds/10* | | | |
|---|---|---|---|---|
| Treatment | 3 days | 7 days | 14 days | 30 days |
| Greene Countrie Ent. "Fire Ant Hayter Bait: | $0.33^b$ | $0.00^b$ | $0.33^b$ | $0.00^b$ |
| Ortho ® Orthene ® | $0.67^b$ | $0.00^b$ | $0.33^b$ | $0.33^b$ |
| Untreated control | $5.67^a$ | $4.67^a$ | $4.00^a$ | $4.33^a$ |

*Means followed by the same letter within the same column were not significantly different using Analysis of Variance (ANOVA) and means separated using Duncan's Multiple Range test at $p \leq 0.05$ (SPSS, Windows 14.0).

TABLE 3

Mean number of imported fire ant mounds per average (mean) treatment plot area, treated October 2, 2007, Brazos County, TX.

| Treatment | Mean no. Active ant mounds/plot* 30 days |
|---|---|
| Greene Countrie Enterprises "Fire Ant Hayter Bait" | 1.67[b] |
| Ortho ® Orthene ® | 4.33[ab] |
| Untreated control | 9.33[a] |

*Means followed by the same letter within the same column were not significantly different using Analysis of Variance (ANOVA) and means separated using Duncan's Multiple Range test at $p \leq 0.05$ (SPSS, Windows 14.0).

What is claimed is:

1. A pesticide composition for exterminating insects comprising:
    at least one attractant wherein the attractant is blood meal, gelatin, sugar, fruit gelatin, corn meal, tortilla mix or a mixture thereof;
    at least one plant growth stimulant comprising blood meal; diatomaceous earth;
    an organophosphorous insecticide wherein said insecticide is between 1 and 6 weight percent of said composition total weight of a dry mixture of the attractant, the plant growth stimulant, and the insecticide; and
    said attractant, said plant growth stimulant, and said oranophosphous insecticide forming a dry mixture.

2. The composition as defined in claim 1, wherein said at least one attractant is between 2 and 10 weight percent of said composition total weight.

3. The composition as defined in claim 1, wherein said at least one attractant is between 2 and 12 weight percent of said composition total weight.

4. The composition as defined in claim 1, wherein said at least one plant growth stimulator includes a nitrogen containing compound.

5. The composition as defined in claim 1, wherein said blood meal is between 22 and 32 weight percent of said composition total weight.

6. The composition as defined in claim 1, wherein said organophosphorous compound is comprised of acetylphosphoramidothiotic acid O, S-dimethyl ester.

7. The composition as defined in claim 6 wherein said acetylphosphoramidothiotic acid O,S-dimethyl ester is between 1 and 6 weight percent of said composition total weight and said blood meal is between 22 and 32 weight percent of said composition total weight and gelatin is between 2 and 10 weight percent of said composition total weight.

8. The composition as defined in claim 7, the composition further comprising:
    corn meal comprising 29 to 39 weight percent of the flowable powder;
    diatomaceous earth comprising 15 to 28 weight percent of the flowable powder;
    sugar comprising 2 to 12 percent of the flowable powder; and
    tortilla mix comprising 2 to 8 percent of the flowable powder.

9. A pesticide composition for exterminating insects comprising: at least one attractant wherein the attractant is blood meal, gelatin, sugar, fruit gelatin, corn meal, tortilla mix or a mixture thereof;
    at least one plant growth stimulant comprising blood meal; diatomaceous earth; and
    an organophosphorous insecticide wherein said insecticide is between 1 and 6 weight percent of said composition total weight of a dry mixture of the attractant, the plant growth stimulant and the insecticide.

* * * * *